United States Patent
Bell

(10) Patent No.: US 11,131,669 B2
(45) Date of Patent: Sep. 28, 2021

(54) SEALED LATERAL FLOW DEVICE

(71) Applicant: IDEXX Laboratories, Inc., Westbrook, ME (US)

(72) Inventor: Wayne Antony Bell, Kennebunk, ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 0 days.

(21) Appl. No.: 16/609,662

(22) PCT Filed: Apr. 20, 2018

(86) PCT No.: PCT/US2018/028545
§ 371 (c)(1),
(2) Date: Oct. 30, 2019

(87) PCT Pub. No.: WO2018/204097
PCT Pub. Date: Nov. 8, 2018

(65) Prior Publication Data
US 2020/0064343 A1    Feb. 27, 2020

Related U.S. Application Data

(60) Provisional application No. 62/500,279, filed on May 2, 2017.

(51) Int. Cl.
*G01N 33/558* (2006.01)
*B01L 3/00* (2006.01)

(52) U.S. Cl.
CPC ............. *G01N 33/558* (2013.01); *B01L 3/50* (2013.01)

(58) Field of Classification Search
CPC .............. B01L 3/50; B01L 2300/0825; B01L 2300/041; B01L 2300/044; B01L 2300/10; B01L 2300/105; G01N 33/558; G01N 33/54366
See application file for complete search history.

(56) References Cited

U.S. PATENT DOCUMENTS

| | | | |
|---|---|---|---|
| 4,444,879 A * | 4/1984 | Foster | G01N 33/545 422/400 |
| 5,234,813 A * | 8/1993 | McGeehan | B01L 3/502715 422/404 |
| 6,406,922 B2 | 6/2002 | Casterlin et al. | |
| 7,097,983 B2 | 8/2006 | Markovsky et al. | |
| 7,323,139 B2 | 1/2008 | Laborde et al. | |
| 2001/0023075 A1* | 9/2001 | Wong | G01N 33/54366 436/514 |
| 2002/0001818 A1 | 1/2002 | Brock | |
| 2015/0024514 A1 | 1/2015 | Stadthagen et al. | |
| 2016/0053293 A1 | 2/2016 | Broder et al. | |
| 2016/0169881 A1 | 6/2016 | Nazareth et al. | |

* cited by examiner

*Primary Examiner* — Christopher L Chin
(74) *Attorney, Agent, or Firm* — McDonnell Boehnen Hulbert & Berghoff LLP

(57) ABSTRACT

A sealed lateral flow device includes a test strip, a base structure, and a removable cover fixed to the base structure. The test strip includes one or more of a sample application zone, a detection zone, and a liquid collection zone. The test strip is disposed within a bottom section of the base structure. The removable cover fixed to the base structure sealingly encloses the test strip within the base structure and forms an airtight seal of the base structure.

21 Claims, 2 Drawing Sheets

SEALED LATERAL FLOW DEVICE

CROSS-REFERENCE TO RELATED APPLICATION

This application is a U.S. National Phase Application under 35 U.S.C. § 371 of International Application No. PCT/US2018/028545, filed Apr. 20, 2018, which claims the benefit of U.S. Provisional Application No. 62/500,279, filed May 2, 2017, which are explicitly incorporated by reference herein in their entirety.

BACKGROUND

Field

This disclosure generally related to devices for lateral flow assays that allow for detection of a target analyte within a biological or other liquid sample.

Background

Generally, lateral flow testing devices are used in a variety of diagnostic applications. For example, test strips within a lateral flow device may be exposed to samples of saliva, blood, urine, or another biological sample, and specific reagents on the test strip or strips are designed to react with the sample to provide a signal when a certain target analyte is present (or not present) in the sample.

Traditionally, lateral flow testing devices are sealed within a foil or other impermeable bag with a moisture absorbent packet inside the bag to ensure that a test strip or test strips within the bag are not exposed to moisture that may prevent proper performance of the device. The existing, traditional packaging and design of such devices results in an inefficient use of packaging materials and storage space.

Accordingly, the inventor has identified a need for an improved design of lateral flow testing devices that reduces the size of the packaging, reduces overall material usage and costs, and reduces overate waste, among other benefits.

SUMMARY

In one aspect, the disclosure is directed to a sealed lateral flow device. The lateral flow device includes a test strip, or strips, a base structure, and a removable cover. The test strip includes one or more of a sample application zone, a detection zone, and a liquid collection zone. Furthermore, the test strip is disposed within the bottom section of the base structure. The removable cover is fixed to the based structure and sealingly encloses the test strip within the base structure. Moreover, the removable cover also forms an airtight seal with the base structure. In various embodiments, the sealed lateral flow device may further include a desiccant or other moisture absorber that is enclosed within the airtight seal when the removable cover is fixed to the base structure. Within embodiments described, the removable cover is peelable from the base structure.

In further embodiments, the removable cover is fixed to an outer edge of the base structure. In some examples, the outer edge of the base structure may extend beyond a height of a test strip cover that is coupled the base structure and covers a test strip located within the sealed lateral flow device. As such, among some examples, a space is formed between the removable cover sealed to the base structure and the test strip cover. The test strip cover overlays and covers the test strip and includes at least one opening at an application zone of the test strip, and in some examples, another opening at a detection zone of the test strip.

In additional aspects, a container includes a plurality of the sealed lateral flow devices and the sealed lateral flow devices are arranged in a packaged product that includes the container without any further covering or packaging.

In yet further embodiments, a lateral flow assay device is described. The lateral flow assay device includes a six-sided unit that has a top portion, a bottom portion and four side portions. The lateral flow assay device further includes at least one lateral flow matrix member disposed within the six-sided device. Additionally, a moisture impervious member is removably secured to a sealing edge disposed on an outer periphery of the top portion of the unit. Among other aspects, the at least one lateral flow matrix member includes at least one reagent useful for performing an immunoassay.

These as well as other aspects, advantages, and alternatives, will become apparent to those of ordinary skill in the art by reading the following detailed description, with reference where appropriate to the accompanying drawings.

DESCRIPTION

Figure 1:
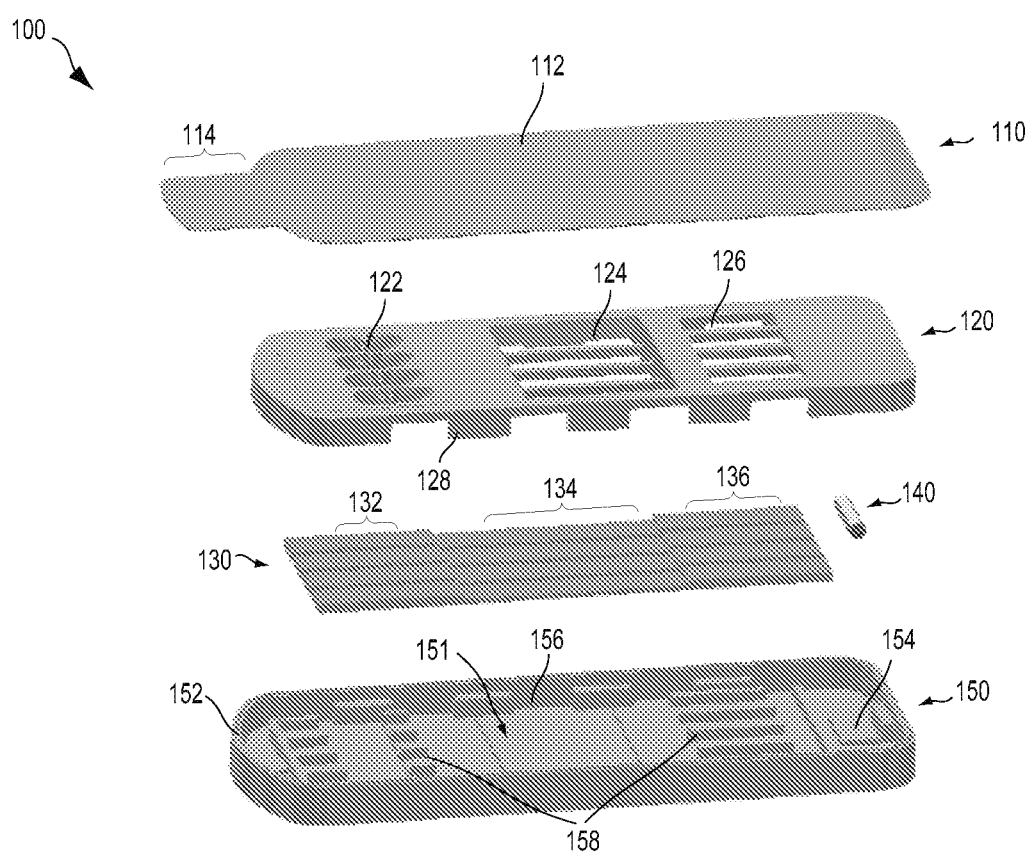
FIG. 1 illustrates an exploded isometric view of a sealed lateral flow device, according to an example embodiment.

Example methods and systems are described herein. The words "example," "exemplary," and "illustrative" are used herein to mean "serving as an example, instance, or illustration." Any embodiment or feature described herein as being an "example," being "exemplary," or being "illustrative" is not necessarily to be construed as preferred or advantageous over other embodiments or features. The example embodiments described herein are not meant to be limiting. It will be readily understood that the aspects of the present disclosure, as generally described herein, and illustrated in the figures, can be arranged, substituted, combined, separated, and designed in a wide variety of different configurations, all of which are explicitly contemplated herein.

In general, the disclosure is directed to lateral flow devices that may be utilized in a variety of diagnostic applications. A lateral flow immunoassay test (also known as an immunochromatography assay, strip test, or other general terms), allows for widespread diagnostic testing of a biological sample for relatively low cost. Such devices are well known in the field of clinical diagnostics and include reagents and binding partners that allow for various assay formats that are well known in the art (sandwich, competition, direct, indirect, etc.). For example, a liquid sample may be placed on one end of a test strip, and through capillary flow the sample may travel laterally across the test strip. Binding partners for the analyte, e.g., antibodies, antigens or aptamers, may be located within the test strip such that as the sample flows, any target analytes that are being tested for within the sample may bind to the binding partner(s). Using an example of a mobilizable antibody that binds an analyte of interest, as the sample continues to flow across the test strip the antibody/target analyte complexes may be immobilized/captured at a detection zone on the strip. The antibodies may be conjugated to a colored particle or other signaling means (e.g., enzyme, fluorescent moiety), that provide a signal to notify a user of the presence, absence, or quantity of the analyte, depending on the format of the assay.

Typically, the test strip that includes the reactive portion of a lateral flow assay device are packaged within a foil or other impermeable bag. Sometimes, the test strip may include a surrounding structure or housing that facilitates simpler use of the test strip for the consumer while also protecting the test strip from becoming damaged. However, even then the supporting structure or housing may be completely encased by a bag or other packaging in order to protect the test strip from inadvertently becoming activated or otherwise becoming damaged. This results in packaging processes that are inefficient and excessively costly because of the amount of material used.

Beneficially, as described herein, an improved sealed lateral flow device reduces the size of packing, reduces the overall material usage, and reduces overall waste. The lateral flow device eliminates the need for an impermeable bag and all the excess packaging previously used. Instead, a low-profile design with airtight sealing features are designed into the lateral flow device structure that houses a test strip. The low-profile design allows for easy packing within a container for shipping of multiple lateral flow devices to stores or consumers. Additionally, less material is required without compromising the integrity of the test strip located within the lateral flow device. As a result of the improved profile and design of the sealed lateral flow device, the air space inside the sealed lateral flow device is less than air typically captured in an externally sealed bag typical of existing devices. Because of the reduced air space within the lateral flow device, the volume of possible moisture within the air inside the sealed lateral flow device is less. With less volume of air to be controlled, a lower volume of moisture absorbing material (e.g., desiccant) is also achieved. By using less material, significant cost savings may be available. Moreover, the design of the lateral flow device described herein makes for a diagnostic testing device that is simple for the consumer to use.

Referring now to the figures, FIG. 1 illustrates an exploded isometric view of a sealed lateral flow device 100, according to an example embodiment. The sealed lateral flow device 100 includes a removable cover 110, a test strip cover 120, a test strip 130, a desiccant 140, and a base structure 150. Within other embodiments, the sealed lateral flow device 100 may include more or less components than depicted in FIG. 1. The removable cover 110 may include a main section 112 and an extended tab section 114. Furthermore, the test strip cover 120 may include a first opening 122, a second opening 124, a third opening 126, and at least one tab 128. The test strip 130 may include one or more of a sample application zone 132, a detection zone 134, and a liquid collection zone 136. Moreover, the base structure 150 may include a bottom section 151, an outer edge 152, a desiccant holder 154, at least one tab slot 156, and at least one test strip slot 158.

A biological or other sample may be applied to the sample application zone 132 of the test strip 130. Within the application zone 132, analytes within the sample may bind to antibodies or other binding partners located on the test strip 130. As such, within examples, the test strip 130 may have at least one reagent or antibody for performing an immunoassay. The sample applied to the test strip 130 may flow from the sample application zone 132 to the detection zone 134. Within examples, the detection zone 134 may be adjacent to the sample application zone 132. At the detection zone 134 the analytes and antibodies may become immobilized and cause a signal to be displayed on the detection zone 134. The detection zone 134 may be adjacent to the liquid collection zone 136. In some aspects, the liquid collection zone 136 may draw the flow of the sample across the test strip 130 via capillary flow.

The sample application zone 132, the detection zone 134, and the liquid collection zone 136 may each have unique physical material properties. Within other examples, the test strip 130 may include additional zones or pads or other components designed to perform some diagnostic function of a biological sample via lateral flow. In some examples, the test strip 130 may be considered a lateral flow matrix. In further examples, the sealed lateral flow device 100 may include more than one test strip 130.

Within examples, the test strip 130 may be located or disposed within the base structure 150 of the sealed lateral flow device 100. More particularly, the test strip 130 may be disposed within the bottom section 151 of the base structure 150. The bottom section 151 may be a primarily flat bottom of the base structure 150 with various protrusions and recesses configured to couple to or be disposed with other components of the sealed lateral flow device 100. For example, the bottom section 151 of the base structure 150 may include at least one test strip slot 158 that is configured to hold the test strip 130 in place within the base structure 150. For example, the at least one test strip slot 158 may include protrusions that extend vertically upwards such that the test strip 130 may fit between such protrusions and thus limit or prevent the movement of the test strip 130 within the base structure 150. In some examples, the at least one test strip slot 158 of the base structure 150 may maintain an alignment of the test strip 130 within the base structure 158. Within examples where there may be more than one test strip 130, there may be a corresponding number of test strip slots, such as the at least one test strip slot 158, in order to align the more than one test strip 130 within the base structure 150.

Additionally, the base structure 150 may include the desiccant holder 154. The desiccant holder 154 may include one or more protrusions extending vertically from the base structure 150 such that the desiccant 140 may be maintained or held within a specific area or portion of the base structure 150. The desiccant 140 may be considered a moisture absorber or other similar component configured to absorb any excess moisture within the base structure 150 or the sealed lateral flow device 100. More particularly, when the sealed lateral flow device 100 is sealed closed, the desiccant 140 may limit an amount of moisture within the sealed lateral flow device 100. The desiccant 140 may be in the form of a bag or a pack that is removable from the sealed lateral flow device 100, among other examples.

In some embodiments, such as depicted in FIG. 1, the base structure 150 may also include the at least one tab slot 156. The at least one tab slot 156 may be a recess or between protrusions of the base structure 150 that is configured to correspond to the at least one tab 128 of the test strip cover 120. As such, the at least one tab 128 and the at least one tab slot 156 may provide means for coupling or otherwise attaching the test strip cover 120 to the base structure 150. In other examples, the test strip cover 120 may be coupled to the base structure 150 with more or less than the number of tabs 128 and slots 156 depicted in FIG. 1. Additionally, various other means of coupling the test strip cover 120 and the base structure 150 are considered herein. For example, the test strip cover 120 may be sized slightly smaller than the base structure 150 such that the test strip cover 120 may fit tightly and/or securely within the base structure 150 without the use of tabs. In such an example, friction between the test strip cover 120 and the base structure 150 may maintain the test strip cover 120 within the base structure 150.

In some examples, the at least one tab 128 may be considered a protrusion extending vertically in a downward direction. The test strip cover 120 may be considered to be removably attached to the base structure 150. Furthermore, the test strip cover 120 may be between the test strip 130 and the removable cover 110. In alternative embodiments, the strip cover 120 includes slots and the base structure 150 includes corresponding tabs.

Within examples, the number of tabs 128 of the test strip cover 120 may directly correspond to the number of tab slots 156 of the base structure 150 in order to facilitate the coupling of the test strip cover 120 to the base structure 150. The at least one tab 128 may bend and/or include additional protrusions that may snap in to corresponding recesses within the base structure 150 and or the at least one slot 156 of the base structure. Within examples, the base structure 150 and the test strip cover 120 may be biased to remain coupled together unless an outside force is applied to one of the test strip cover 120 or the base structure 150 and forces one apart from the other. While FIG. 1 depicts the test strip cover 120 and the base structure 150 assembled via the tabs 128 and slots 156 of the respective components, other configurations to secure the test strip cover 120 to the base structure 150 may be used (e.g., press fit, snap fit, lock and key, and fasteners).

The test strip cover 120 may cover at least one of the sample application zone 132, the detection zone 134, and the liquid collection zone 136 of the test strip 130. Additionally, within embodiments, the test strip cover 120 may include the first opening 122 at the sample application zone 132 and the second opening 124 at the detection zone 134. Further, the test strip cover 120 may include the third opening 126 at the liquid collection zone 136. As depicted in FIG. 1, the first opening 122 may include a set of openings or wells that allow application of a biological test sample to the test strip 130. Furthermore, the second opening 124 may include a set of openings that allow optical or visual access to the detection zone 134 of the test strip 130. In some examples, the second opening 124 at the detection zone 134 includes a window for viewing the test strip 130. As such, a user may be able to see a signal on the test strip 130 through the second opening 124 after application of a sample to the test strip 130 through the first opening 122. The third opening 126 allows for the user to view that the liquid sample has proceeded to the collection zone to ensure that sufficient time has passed before reading a signal from at the second opening 124.

Within examples where the first opening 122 includes a set or series of wells, the number of wells may correspond to a number of test strips 130 that are disposed within the base structure 150 of the sealed lateral flow device 100. As depicted in FIG. 1, the first opening 122 includes four wells, while in other examples the first opening 122 of the test strip cover 120 may include more or less than four wells. Furthermore, the number of wells of the first opening 122 may not correspond to a number of test strips 130. For example, a single well may feed or allow access to more than one test strip. The wells of the first opening 122 may be tapered such that only a certain amount of a sample is exposed to the test strip 130 at a time. The base structure 150 and the test strip cover 120, and any components of each (e.g., the first opening 122 of the test strip cover 120), may be constructed out of molded plastic, among a number of other available materials.

The base structure 150 further includes the outer edge 152. Within examples, the outer edge 152 of the base structure 152 may extend vertically in an upwards direction away from the bottom section 151 of the base structure 150. Furthermore, the outer edge 152 may extend beyond a height of the test strip cover 120. Within examples, the outer edge 152 may be considered a sealing edge of the base structure 150 and may also be disposed along an outer periphery of a top portion of the base structure 150. Additionally, the outer edge 152 may include a lip of material that is integrally molded with the top portion of the base structure 150. In some examples, the lip of material may define a sealing surface along which the removable cover 110 is coupled to the base structure 150.

The removable cover 110 may be coupled to the base structure 150 at the outer edge 152. Within examples, the removable cover 110 may be coupled to the sealing edge of the base structure 150. Additionally, the removable cover 110 may be detachably sealed or bonded to the base structure 150 of the sealed lateral flow device. More particularly, the main section 112 of the removable cover 110 may be sealingly engaged to the base structure 150 along the outer edge 152. Moreover, the extended tab section 114 of the removable cover 110 may extend beyond the outer edge 152 of the base structure 150. As such, the removable cover 110 may be fixed to the base structure 150 to sealingly enclose the test strip 130 within the base structure 150 and form an airtight seal of the base structure 150. In addition to forming an airtight seal, the removable cover 110 may be considered a moisture impervious member. In other words, the removable cover 110 may be constructed from a material such that the removable cover is impermeable. The removable cover 110 may be bonded, glued, other otherwise sealed (e.g. heat or sonic sealing) to the base structure 150. Thus, the integrity of the test strip 130 is protected from being exposed to any substances that may interfere with the diagnostic use or function of the test strip 130.

To apply a biological sample to the test strip 130, the removable cover 110 is peelable away from the base structure 150. The extended tab section 114 may be considered an integral tab member that extends beyond the outer periphery of the base structure 150. The extend tab section 114 may be arranged such that a user may easily grab the extended tab section 114 of the removable cover 110 in order to being to peel the removable cover 110 back from the base structure 150.

Within examples, because the outer edge 152 may extend beyond the height of the test strip cover 120, and because the removable cover 110 is sealed to the outer edge 152 of the base structure, the test strip cover 120 and the test strip 130 may be arranged such that both the test strip cover 120 and the test strip 130 are spaced away from the removable cover 110. Spacing the removable cover 110 away from test strip cover 120 may help prevent an interaction between a sealing or bonding material used between the removable cover 110 and the base structure 150.

Figure 2:
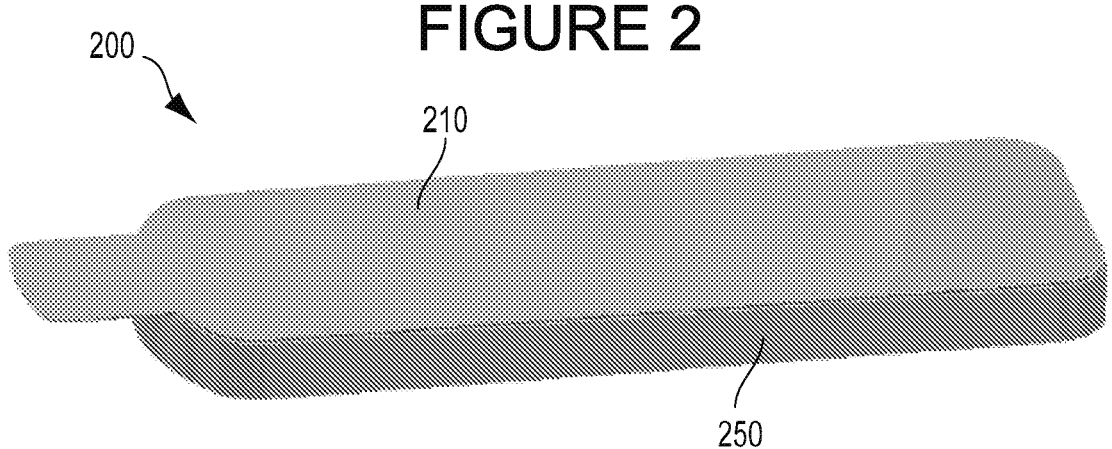
FIG. 2 illustrates a sealed lateral flow device, according to an example embodiment.

Continuing with the Figures, FIG. 2 illustrates a sealed lateral flow device 200, according to an example embodiment. The sealed lateral flow device 200 includes a removable cover 210 and a base structure 250. Although not shown in the view of FIG. 2, the sealed lateral flow device 200 may include additional components similar in form and function to those components included in the sealed lateral flow device 100 of FIG. 1. For example, the sealed lateral flow device 200 may further include a test strip cover and at least one test strip among other possible components.

As depicted in FIG. 2, the removable cover 210 may be removably or detachably secured to the base structure 250. More particularly, the removable cover 210 may be sealed to an outer edge of a top portion of the base structure 250 such that a moisture tight seal is formed. The sealed lateral flow device 200 has a low-profile design highlighted in FIG. 2. As such, with the low-profile design, a plurality of the sealed lateral flow devices 200 may be arranged, organized, or stacked easily within a container or store shelf. Additionally, the removable cover 210 may be a primarily flat surface such that marketing, safety, or other information may be easily displayed on the sealed lateral flow device 200 itself. Thus, a packaged product may include a container with a plurality of the sealed lateral flow devices without the need for any additional covering or materials in order to ship, display, or handle the sealed lateral flow device 200. Each sealed lateral flow device 200 within the product may be easily arranged within a box or other shipping container.

Figure 3:
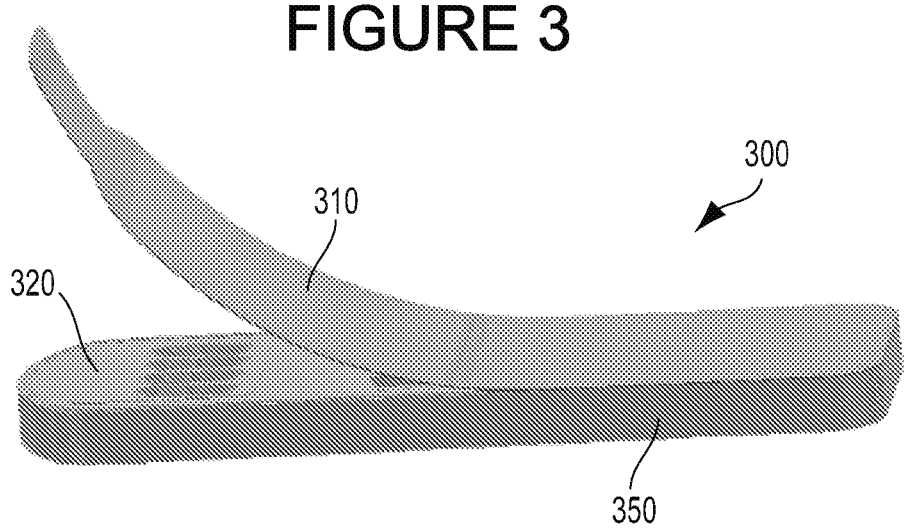
FIG. 3 illustrates a sealed lateral flow device with a removable cover partially peeled back, according to an example embodiment.

Continuing to FIG. 3, FIG. 3 illustrates a sealed lateral flow device 300 with a removable cover 310 partially peeled back, according to an example embodiment. The sealed lateral flow device 300 includes the removable cover 310, a test strip cover 320, and a base structure 350. Although not shown in the view of FIG. 3, the sealed lateral flow device 300 may include additional components similar in form and function to those components included in the sealed lateral flow device 100 of FIG. 1 and/or the sealed lateral flow device 200 of FIG. 2. For example, the sealed lateral flow device 200 may further include at least one test strip and a moisture absorber, among other possible components.

As depicted in FIG. 3, the removable cover 300 may be peeled back from an outer edge of the base structure 350. Although it may be difficult to determine based on the view of FIG. 3, a spacing between the removable cover 310 and the test strip cover 320 may exist between the components to limit any possible interaction of the test strip and/or the test strip dover and a sealing material used to bond the removable cover 310 to the base structure 350.

Within examples, the sealed lateral flow device 300 may be considered a six-sided unit having a top portion, bottom portion and four side portions. Furthermore, the four side portions may include two, substantially parallel sides and two substantially parallel ends. The sides and ends may meet at substantially right angles. In other examples, the four side portions may include two, substantially parallel sides and at least one arcuate end.

CONCLUSION

The present disclosure is not to be limited in terms of the embodiments described in this application, which are intended as illustrations of various aspects. Many modifications and variations can be made without departing from its scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims.

In the figures, similar symbols typically identify similar components, unless context dictates otherwise. The example embodiments described herein and in the figures are not meant to be limiting. Other embodiments can be utilized, and other changes can be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

What is claimed is:

1. A device, comprising:
    a test strip comprising at least one of a sample application zone, a detection zone, and a liquid collection zone;
    a base structure comprising a bottom section, wherein the test strip is disposed within the bottom section;
    a test strip cover coupled to the base structure, wherein the test strip cover covers the at least one of the sample application zone, the detection zone, and the liquid collection zone and comprises an opening for at least one of the sample application zone and the detection zone, and
    a removable cover fixed to an outer edge of the base structure that extends beyond a height of the test strip cover and that sealingly encloses the test strip within the base structure and forms an airtight seal of the base structure.

2. The device of claim 1, further comprising a desiccant located in the base structure and enclosed within the airtight seal.

3. The device of claim 1, wherein the removable cover is peelable from the base structure.

4. The device of claim 1, wherein the test strip cover is detachably coupled to the base structure.

5. The device of claim 1, wherein the test strip cover comprises:
    a first opening at the sample application zone that allows application of a test sample to the test strip, and
    a second opening at the detection zone that allows optical or visual access to the detection zone.

6. The device of claim 5, wherein the second opening comprises a window.

7. The device of claim 1, wherein the removable cover comprises:
    a main section that is sealingly engaged to an outer edge of the base structure; and
    an extended tab section that extends beyond the outer edge of the base structure.

8. The device of claim 1, wherein the test strip cover comprises a protrusion, and further wherein the base structure further comprises a slot such that the protrusion of the test strip cover is inserted into to the slot of the base structure when the test strip cover is coupled to the base structure.

9. The device of claim 1, wherein the bottom section of the base structure comprises a slot to dispose the test strip within.

10. A packaged product comprising a container comprising a plurality of the devices of claim 1, wherein each device is arranged in the container in the absence of a further covering for the device.

11. A device, comprising:
    a test strip comprising at least one of a sample application zone, a detection zone, and a liquid collection zone;
    a base structure comprising a bottom section, wherein the test strip is disposed within the bottom section;
    a removable cover fixed to the base structure that sealingly encloses the test strip within the base structure and forms an airtight seal of the base structure; and
    a test strip cover arranged within the base structure such that the test strip cover is spaced away from the removable cover, wherein the test strip cover covers the at least one of the sample application zone, the detection zone, and the liquid collection zone and comprises an opening for at least one of the sample application zone and the detection zone.

12. The device of claim 11, further comprising a desiccant located in the base structure and enclosed within the airtight seal.

13. The device of claim 11, wherein the removable cover is peelable from the base structure.

14. The device of claim 11, wherein the test strip cover that is detachably coupled to the base structure.

15. The device of claim 11, wherein the removable cover is coupled to an outer edge of the base structure that extends beyond a height of the strip cover.

16. The device of claim 11, wherein the test strip cover comprises:
    a first opening at the sample application zone that allows application of a test sample to the test strip, and
    a second opening at the detection zone that allows optical or visual access to the detection zone.

17. The device of claim 16, wherein the second opening comprises a window.

18. The device of claim 11, wherein the removable cover comprises:
    a main section that is sealingly engaged to an outer edge of the base structure; and
    an extended tab section that extends beyond the outer edge of the base structure.

19. The device of claim 11, wherein the test strip cover comprises a protrusion, and further wherein the base structure further comprises a slot such that the protrusion of the test strip cover is inserted into to the slot of the base structure when the test strip cover is coupled to the base structure.

20. The device of claim 11, wherein the bottom section of the base structure comprises a slot to dispose the test strip within.

21. A packaged product comprising a container comprising a plurality of the devices of claim 11, wherein each device is arranged in the container in the absence of a further covering for the device.

* * * * *